(12) United States Patent
Euzen et al.

(10) Patent No.: US 10,022,547 B2
(45) Date of Patent: *Jul. 17, 2018

(54) ACTIVE IMPLANTABLE MEDICAL DEVICE FOR THE DIAGNOSIS OF CARDIAC DECOMPENSATION

(71) Applicant: SORIN CRM SAS, Clamart (FR)

(72) Inventors: Marie-Anne Euzen, Bierves (FR); Paola Milpied, Paris (FR)

(73) Assignee: Sorin CRM SAS, Clamart (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/701,245

(22) Filed: Sep. 11, 2017

(65) Prior Publication Data
US 2017/0368353 A1  Dec. 28, 2017

Related U.S. Application Data

(63) Continuation of application No. 15/086,938, filed on Mar. 31, 2016, now Pat. No. 9,757,568.

(30) Foreign Application Priority Data

Apr. 2, 2015 (FR) .................................. 15 52843

(51) Int. Cl.
*A61N 1/00* (2006.01)
*A61N 1/368* (2006.01)
(Continued)

(52) U.S. Cl.
CPC .......... *A61N 1/3684* (2013.01); *A61B 5/0422* (2013.01); *A61N 1/056* (2013.01); *A61N 1/0563* (2013.01); *A61N 1/3682* (2013.01)

(58) Field of Classification Search
USPC ...................................................... 607/9, 25
See application file for complete search history.

(56) References Cited

U.S. PATENT DOCUMENTS

2006/0253164 A1  11/2006  Zhang et al.
2007/0043394 A1  2/2007  Zhang et al.
(Continued)

FOREIGN PATENT DOCUMENTS

EP    1 108 446 A1    6/2001
EP    2 105 843 A1    9/2009
(Continued)

OTHER PUBLICATIONS

Milpied, et al., Arrhythmia Discrimination in Implantable Cardioverter Defibrillators Using Support Vector Machines Applied to a New Representation of Electrograms, IEEE Transactions on Biomedical Engineering, vol. 58, No. 6, Jun. 2011, 7 pages.
(Continued)

*Primary Examiner* — Nicole F Johnson
(74) *Attorney, Agent, or Firm* — Foley & Lardner LLP

(57) ABSTRACT

The disclosure relates to a device including a plurality of electrodes for stimulation of both ventricles with application of an atrioventricular delay and of an interventricular delay, a processor configured to multidimensionally measure an interventricular conduction delay, and monitor the evolution of a patient's condition. For the multidimensional measurement of the interventricular conduction delay, the device produces stimulation of one of the ventricles and collects, in the other ventricle, two endocardial electrogram signals on separate respective channels, giving two respective temporal components. Both temporal components are combined in one single parametric 2D characteristic representative of the cardiac cycle, and a comparison is made with reference descriptors for deriving an index representative of the evolution of the patient's condition.

20 Claims, 5 Drawing Sheets

(51) Int. Cl.
*A61B 5/042* (2006.01)
*A61N 1/05* (2006.01)

(56) References Cited

U.S. PATENT DOCUMENTS

| | | |
|---|---|---|
| 2007/0239037 A1 | 10/2007 | Ghio et al. |
| 2008/0294217 A1 | 11/2008 | Lian et al. |
| 2011/0152660 A1 | 6/2011 | Davenport et al. |
| 2012/0165892 A1* | 6/2012 | Min .................... A61N 1/36585 607/25 |
| 2012/0253419 A1* | 10/2012 | Rosenberg ........... A61B 5/0452 607/25 |

FOREIGN PATENT DOCUMENTS

| | | |
|---|---|---|
| EP | 2 324 885 A1 | 5/2011 |
| EP | 2 357 020 | 8/2011 |
| EP | 2 368 493 A1 | 9/2011 |
| EP | 2 737 925 | 6/2014 |
| EP | 2 742 971 | 6/2014 |
| EP | 2 742 973 | 6/2014 |
| EP | 2 839 859 | 2/2015 |

OTHER PUBLICATIONS

Preliminary Search Report for French Patent Application No. 1552843, dated Jan. 19, 2016, 2 pages.

* cited by examiner

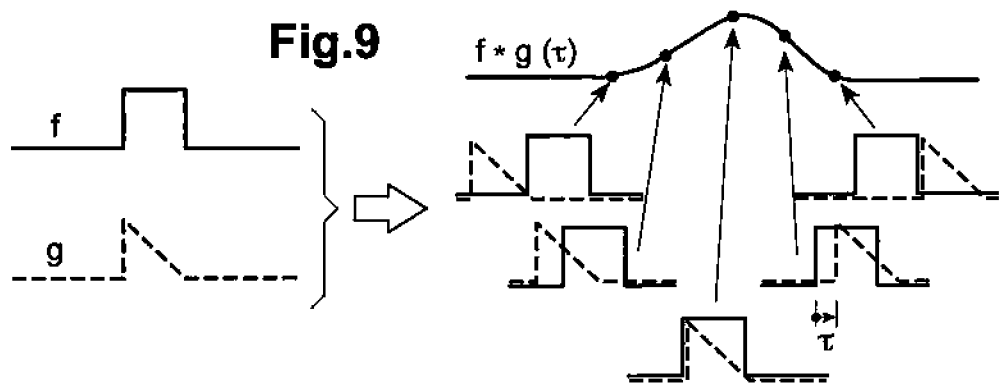
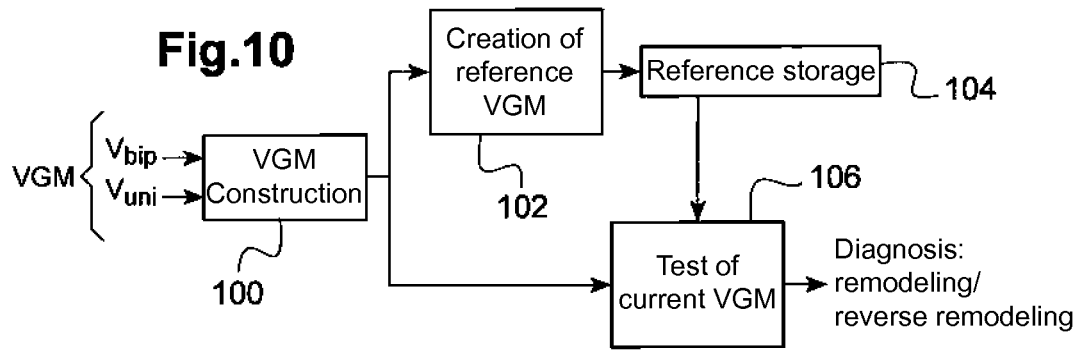
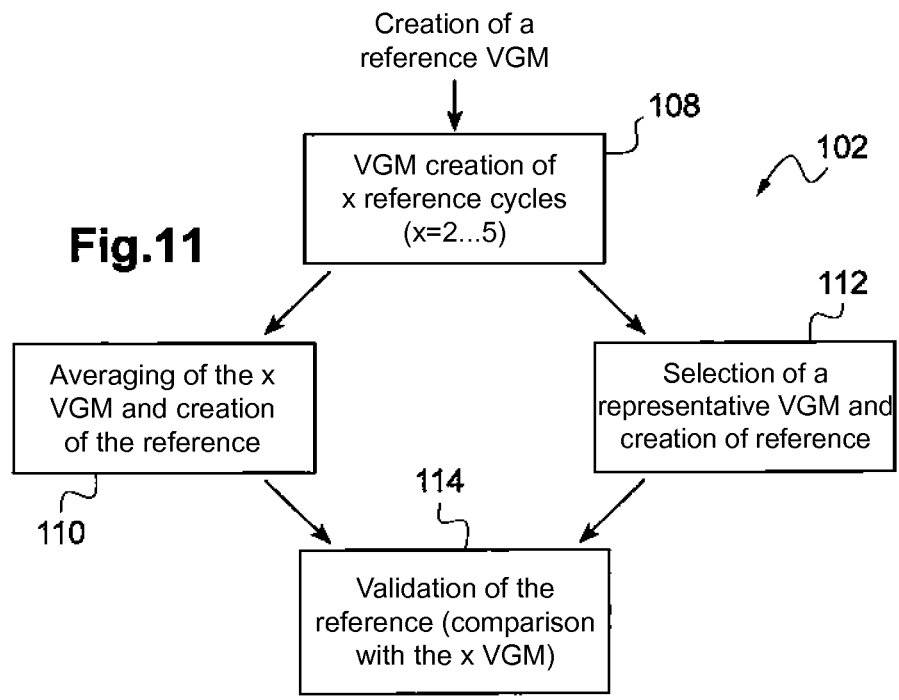

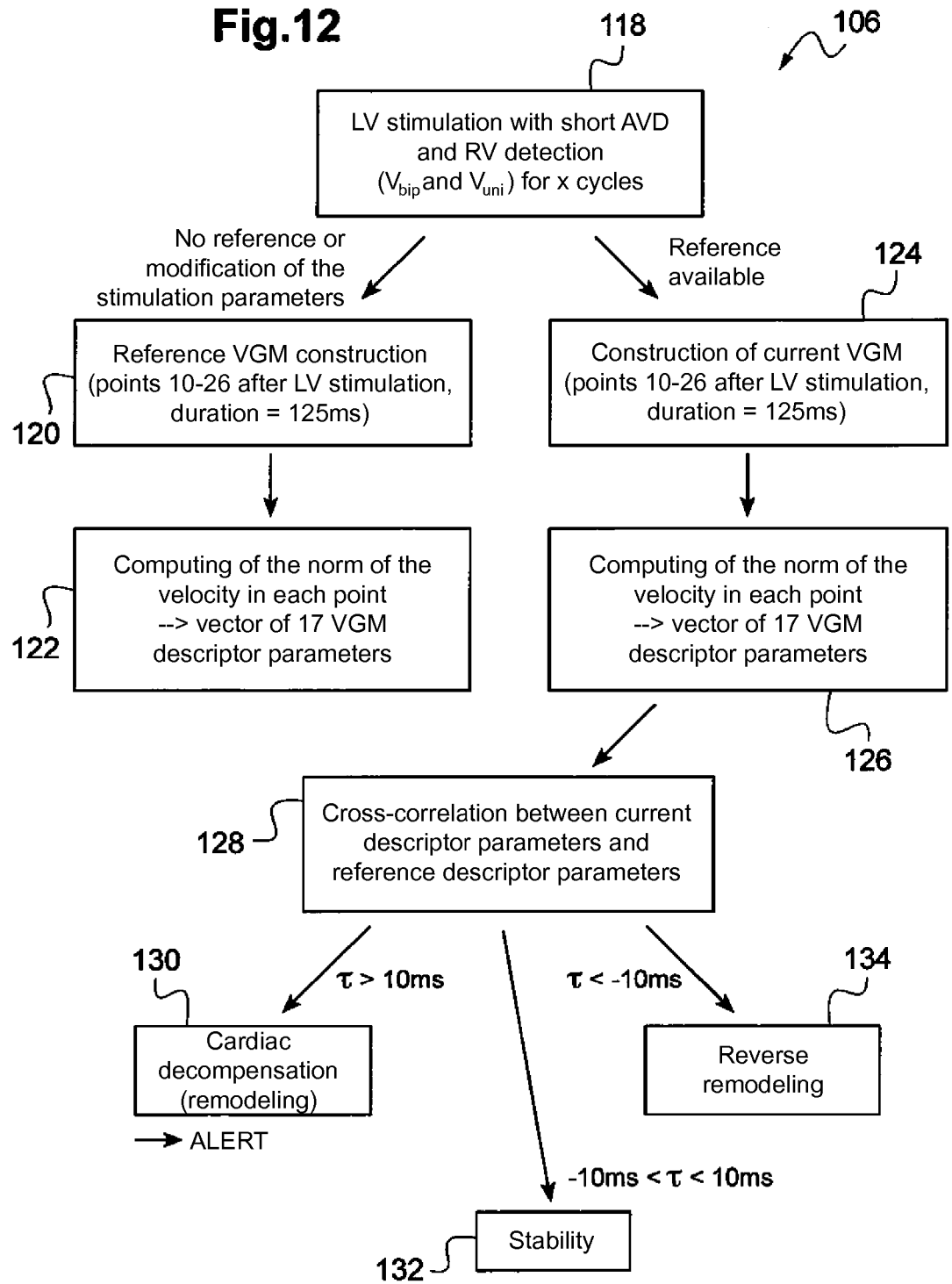

ACTIVE IMPLANTABLE MEDICAL DEVICE FOR THE DIAGNOSIS OF CARDIAC DECOMPENSATION

CROSS-REFERENCE TO RELATED PATENT APPLICATIONS

This application is a continuation of U.S. patent application Ser. No. 15/086,938, now U.S. Pat. No. 9,757,568, filed Mar. 31, 2016, which claims the benefit of and priority to French Patent Application No. 1552843, filed Apr. 2, 2015, each of which is incorporated herein by reference in its entirety.

BACKGROUND

The disclosure relates to "active implantable medical devices" as defined by Directive 90/385/EEC of 20 Jun. 1990 of the Council of the European Communities.

It more precisely relates to implants that continuously monitor a cardiac rhythm and deliver to the heart, if necessary, electrical pulses to jointly and permanently stimulate the left and right ventricles to resynchronize them, a technique called "CRT" (Cardiac Resynchronization Therapy) or "BVP" (Bi-Ventricular Pacing).

A CRT pacemaker is disclosed for example in EP 1108446 A1 (Sorin CRM), which describes a device for applying stimulation between the respective contractions of the left and right ventricles, creating a variable delay called "interventricular delay" (VVD), which is adjusted to resynchronize the contraction of the ventricles with fine optimization of the patient's hemodynamic status. The VVD can be zero, positive (the left ventricle is stimulated after the right ventricle) or negative (the right ventricle is stimulated after the left ventricle).

CRT devices also include a "dual chamber operating" mode in which the device monitors the ventricular activity after a spontaneous (detection of an atrial depolarization P wave) or stimulated (application of an atrial pulse A) atrial event. At the same time, the device starts timing a delay called "an atrioventricular delay" (AVD) such that if no ventricular spontaneous activity (R wave) has been detected at the end of this period, the device triggers a stimulation of the ventricle (application of a ventricle V pulse).

The general object of the present V disclosure is, in this context, to measure an interventricular conduction time, i.e., the time interval between a stimuli applied to one of the ventricles and induced spontaneous contraction in the other ventricle by this stimulation (note that in this particular configuration of measurement, both ventricles are no longer stimulated jointly).

Changes to the interventricular conduction time in the long term may be a good indicator of the evolution of the patient's cardiac condition, including the phenomenon known as "cardiac remodeling," which can be defined as all the changes of the heart caused in response to a disease, which is generally associated with a worsened prognosis.

The clinical changes may be asymptomatic, it is common that the patient unconsciously adapts its activity to his/her clinical status. For example, due to stress, the first heart failure attack symptoms may appear, leading the patient to reduce his activity to prevent the occurrence of such crises. The symptoms may not appear anymore because the patient changed his/her behavior to avoid them, but the disease continues to progress.

Remodeling occurs, in the long term, by increasing the volume of the left ventricle, with deterioration in the ejection fraction and of the intraventricular pressure regime due to the decrease of contractility and/or to excessive pressure downstream and, ultimately, a decrease in cardiac output. This may cause serious consequences on the organism by the progression of heart failure. It is generally only when the heart failure hinders the patient at rest that he/she will consult or, in extreme cases, be admitted to a hospital.

In summary, due to this self-adjustment, the absence of symptoms experienced introduces a significant delay between the onset of clinical changes and diagnosis of these changes, which is often made too late.

By stimulating the ventricles in a controlled method in at least two points, the CRT therapy optimizes the contraction/relaxation cycle, with a direct benefit to facilitate the heart work, which can help stabilize the remodeling phenomenon, and even counter it ("reverse remodeling"), with an improved prognosis for the patient.

One object of the disclosure is to provide a diagnostic tool, embedded in a CRT pacemaker, that would provide regular monitoring (e.g. daily) of the patient's condition, especially the evolution of a cardiac remodeling or of a reverse remodeling. The monitoring occurs during an early stage, to be able to rapidly take appropriate measures, such as a change in the configuration of the CRT therapy, or switching from this CRT therapy to another one, if is not effective. This avoids the unexpected triggering, in the short or medium term, of a crisis.

The current technique for the evaluation of the patient's condition, and therefore for the evaluation of the CRT therapy and adjustment of CRT pacing parameters, is evaluated by echocardiography with the measurement of the ventricular volume and the estimate of the characteristic delays of the systole, in particular the opening delay of the aortic valve. This procedure must, however, be implemented in hospitals and by qualified personnel, as it is long and expensive and cannot be applied as often as would be useful or necessary without interfering with the patient's daily life.

The measurement at regular intervals (e.g., daily) of the interventricular conduction delay and the long term monitoring of this data allows a diagnosis of a favorable reverse ventricular remodeling, indicating that the CRT therapy is effective, or vice versa a deleterious ventricular remodeling, indicating a degradation of the patient's condition.

Automatic analysis techniques from the implantable device have also been proposed, for example in US 2011/0152660 A1, now U.S. Pat. No. 8,249,709, wherein degradation and improving of the condition of the patient are evaluated from the evolution of the interventricular delay, considered alone or in combination with the evaluation of the patient's activity and/or the presence of pulmonary edema. The interventricular conduction delay is measured using endocardial or epicardial left and right ventricular electrodes. However, this method is very sensitive to the position of the leads, a variation of, for example, 20% of the interventricular conduction delay being equated with the detection of the displacement of a lead. This technique is also sensitive to the method by which the heart remodels, so that in some cases the measured ventricular conduction delay may not provide the sought remodeling information. This may happen especially if no significant change in the conduction delay is observed along the axis of measurement (between the single electrode on the right and the single electrode on the left), while according to another axis a much larger variation could have been observed.

US 2007/0239037 A1 discloses another method based on the measurement of the interventricular conduction delay (as determined by ultrasound) before implantation of the device, which aims to predict the response of a patient to a CRT therapy. The greater the initial interventricular conduction delay, the higher chance a major remodeling is likely to occur. However, this is a prediction tool requiring a scan at an initial time, not a diagnostic tool to assess the long term evolution of a patient's condition, after implantation of the CRT device.

US 2007/0043394 A1, now U.S. Pat. No. 8,494,618, describes a technique for diagnosis of heart failure by detection of a variation of the intracardiac impedance at a constant heart rate. The evolution of this parameter in the long term can infer if the heart remodels or not. However, the measurement of the intracardiac impedance is not a stable parameter in the long term (several weeks or even months), which renders the use difficult for diagnostic purposes with a sufficient degree of reliability.

SUMMARY

According to some embodiments, a CRT implantable device is provided with diagnosis methods of cardiac remodeling to overcome the aforementioned drawbacks, and in particular:

To consider at least two measurement axes in order to obtain a more robust measure of the interventricular delay (a measure designated as "multidimensional measure of interventricular conduction delay");

To avoid long and costly echocardiogram examinations, which provide only a late diagnosis, often several months after implantation;

To quickly and robustly assess patient remodeling to adapt the resynchronization therapy (possible adjustment of the AVD and/or of the VVD);

To set up alerts in case of risk of decompensation or of worsened ischemia to prevent hospitalizations and modify in due time the therapies and treatments; and In general, to ensure proper delivery and effectiveness of CRT therapy.

More specifically, embodiments of the disclosure provide a cardiac resynchronization therapy device by biventricular stimulation including:

Methods of detection of atrial and ventricular events;

Methods of stimulation of the right and left ventricles, with the application i) of an atrioventricular delay (AVD) between a spontaneous or stimulated atrial event and stimulation of the right ventricle, and ii) an interventricular delay (VVD) between the respective times of stimulation of the right and left ventricles;

Methods of multidimensional measurement of the interventricular conduction delay, counted between a stimulation of the right or the left ventricle and a spontaneous event detected in the left ventricle, or vice versa, or between a stimulation of the right ventricle and a spontaneous event detected between right and left ventricles in the same cardiac cycle; and Methods of monitoring of the evolution of a patient's condition, adapted to store a history of the measured conduction delays at successive dates and to derive an representative index.

In some embodiments, the methods of multidimensional measuring of the interventricular conduction delay may include:

Methods adapted for controlling the stimulation and the sensing during at least one cardiac cycle so as to:
Produce a stimulation of one of the ventricles, and
Collect in the other ventricle, concurrently, on separate respective channels, at least two endocardial electrogram (EGM) signals and derive at least two respective distinct temporal components;

Methods adapted to combine the at least two temporal components in at least one 2D parametric characteristic representative of the cardiac cycle, based on variations of one of the temporal components as a function of the other;

Methods of analysis, adapted to derive from the 2D characteristic, or an average of 2D characteristics collected over successive cardiac cycles, a vector of current intrinsic descriptor parameters of the 2D characteristic; and Comparator methods adapted to compare said vector of current descriptor parameters to a homologous vector of reference descriptor parameters for deriving an index representative of the evolution of a patient's condition.

According to various advantageous embodiments:

The intrinsic descriptor parameters are parameters function of the velocity vector of the 2D characteristic considered in a plurality of respective points of this characteristic, in particular the respective values of the norm of the velocity vector;

The comparator methods include methods to operate a cross-correlation between i) the vector of current descriptor parameters and ii) the vector of reference descriptor parameters;

The index representative of the evolution of a patient's status is the value of the delay which maximizes the intercorrelation function between the vector of current descriptor parameters and the vector of reference descriptor parameters, this delay being, in particular possibly compared to a predetermined threshold to trigger an alert when this threshold is crossed;

The device further includes methods able to temporarily shorten the atrioventricular delay of the device during the activation of the multidimensional measuring of the ventricular conduction delay;

The device further includes methods able to temporarily force the activation of atrial pacing during the activation of multidimensional measurement of the interventricular conduction delay;

The at least two EGM signals concurrently collected on separate respective channels include:
A unipolar far-field EGM signal ($V_{uni}$) collected between:
i) proximal or distal electrode or, where appropriate, an intermediate electrode or the defibrillation coil of a ventricular lead located in the not stimulated ventricle and ii) the metal housing of the generator of the device, or
i) a first proximal electrode, or a distal electrode or defibrillation coil and ii) a second proximal electrode, or a distal electrode or, where appropriate, an intermediate electrode or a defibrillation coil, respectively of two separate ventricular leads located both in the ventricle that is not stimulated, or
i) a first proximal electrode, or a distal electrode or a defibrillation coil and ii) and a second proximal electrode, or a distal electrode or an intermediate electrode, respectively of a right ventricular lead and of a left ventricular lead, and
A bipolar near-field EGM signal collected between:
i) a distal electrode and ii) a proximal electrode of a ventricular lead located in the ventricle that is not stimulated, or i) a defibrillation coil and ii) a distal or proximal electrode of said ventricular lead, or
i) a distal electrode and ii) an intermediate electrode of a left ventricular lead, or
i) a proximal electrode and ii) an intermediate electrode of said left ventricular lead, or
two intermediate electrodes of said left ventricular lead.

BRIEF DESCRIPTION OF THE DRAWINGS

Further features, characteristics and advantages of the present disclosure will become apparent to a person of ordinary skill in the art from the following detailed description of preferred embodiments of the present disclosure, made with reference to the drawings annexed, in which like reference characters refer to like elements and in which:

FIG. 9 illustrates a principle of a cross-correlation processing, applied between the current descriptor parameters and reference descriptor parameters of the analyzed vectograms.

FIG. 10 is a schematic diagram illustrating an implementation of an embodiment of the invention.

FIG. 11 is a diagram showing a sequence of steps executed during the preliminary preparation of references.

FIG. 12 is a diagram showing a sequence of steps performed during a patient follow-up, to determine the evolution of his condition, including a reverse remodeling or a remodeling.

DETAILED DESCRIPTION

An embodiment of the device of the invention will now be described.

Regarding its software aspects, the embodiment of the invention may be implemented by appropriate programming of the controlling software of a known stimulator, for example a cardiac pacemaker, including methods of acquisition of a signal provided by endocardial leads and/or one or several implantable sensors.

The embodiment of the invention may notably be applied to implantable devices, such as that of the Reply, Paradym, Intensia, Paradym RF and Platinium families, manufactured and commercialized by Sorin CRM, Clamart, France.

These devices include programmable microprocessor circuitry to receive, format and process electrical signals collected by implantable electrodes, and deliver stimulation pulses to these electrodes. It is possible to download, by telemetry, software that is stored in memory and executed to implement the functions of the embodiment of the invention that are described below. The adaptation of these devices to the implementation of the functions of the invention is within the skill in the art and will not be described in detail.

A method of the disclosure is implemented primarily by software, by appropriate algorithms automatically and repeatedly executed by a microcontroller or a digital signal processor. For the sake of clarity, the various processing applied are broken down and schematically by a number of distinct functional blocks, but this representation, however, is only for illustrative purposes, these circuits include common elements and correspond in practice to a plurality of functions generally performed by the same software.

Figure 1:
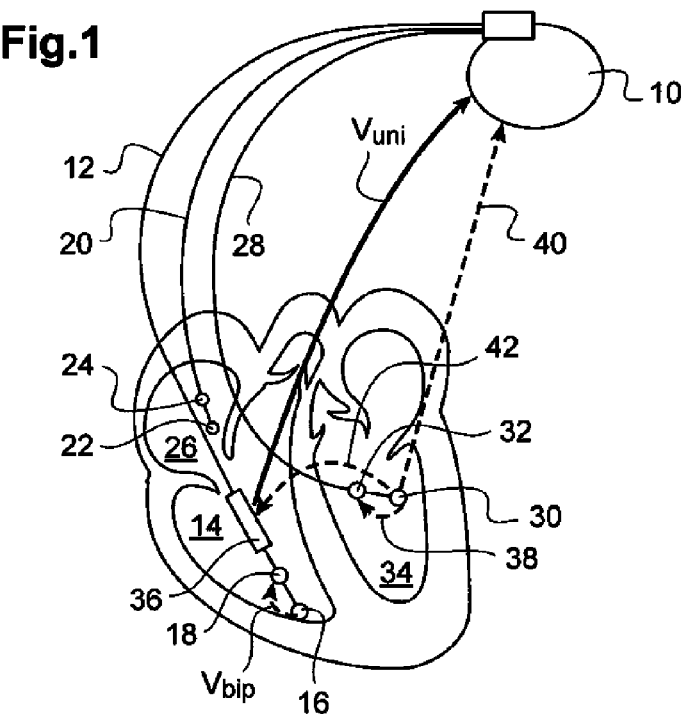
FIG. 1 is a general view showing a CRT device with a generator and right and left cardiac leads implanted in a heart.

FIG. 1 illustrates a stimulation configuration wherein a pulse generator 10 is associated with a first lead 12 located in the right ventricle 14. A head of the lead includes two electrodes, namely a distal electrode (tip) 16 and a proximal electrode (ring) 18. A second lead 20 is provided with distal 22 and proximal 24 electrodes for atrial detection located at the right atrium 26 for the detection of signals in this cavity and to optionally apply atrial stimulation.

To allow bi-ventricular pacing, in particular to restore the synchronization between the two ventricles, the device is provided with a third lead 28, for example a lead disposed in the coronary network, including one or more electrodes 30, 32 disposed in the vicinity of the left ventricle 34. In addition to the illustrated distal and proximal electrodes 30, 32, the left lead may also include one or more intermediate electrodes located in a median position between the electrodes 30 and 32.

It is thus possible to ensure the simultaneous stimulation, or with a controlled slight temporal shift (interventricular delay VVD), of both the right and left ventricles to restore the synchronization between these two cavities and improve overall patient hemodynamics. The right ventricular lead 12 may also be provided with a ventricular coil 36 forming a defibrillation electrode and also be able to collect an endocardial signal (this coil being also able to replace the proximal ring electrode 18).

With specific regard to the stimulation of the left ventricle, it is possible to use a bipolar configuration (between the two electrodes 30 and 32 of the lead 28) or unipolar configuration (between one of the electrodes 30 or 32 and the can housing) of the generator 10. The two corresponding "stimulation vectors" are referenced 38 and 40 in FIG. 1. These same vectors can also be used for collecting a signal of left ventricular depolarization. Note that in the case of a multipolar lead, a large number of bipolar and unipolar possible vectors are possible, defined from each of the electrodes.

One object of the disclosure is to provide monitoring of cardiac remodeling, from the measurement of an interventricular conduction delay:
When the ventricular volume decreases (reverse remodeling, beneficial to the patient), the conduction delay between the ventricles should be shortened;
Conversely, when the heart expands (deleterious remodeling), the conduction delay between the ventricles should increase.

More specifically, to overcome the drawbacks of known techniques that have been recalled in the introduction, the disclosure proposes to combine two endocardial electrogram signals (EGM) from the same ventricular cavity, for example from the right ventricle. These signals result from the depolarization produced through the application of a stimulation on the other ventricle (the left ventricle in this example).

As shown in FIG. 1, the EGMs thus collected in the right ventricle may include:

A right ventricular component $V_{bip}$ derived from a bipolar near-field EGM signal collected between the distal electrode 16 and the proximal electrode 18 of the right ventricular lead 12, and Another right ventricular component $V_{uni}$ derived from a unipolar far-field EGM signal collected between the defibrillation coil 36 of the right ventricular lead 12 and the metal housing of the generator 10.

Figure 2:
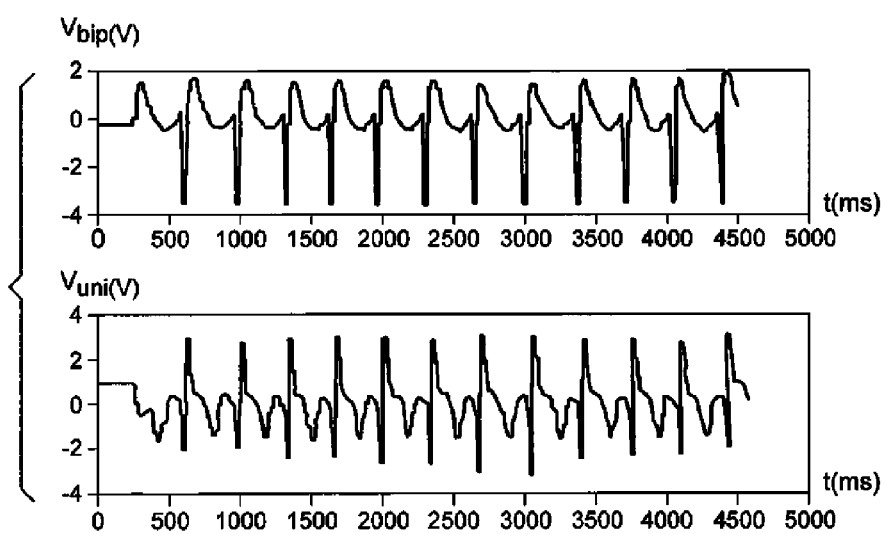
FIG. 2 is an example of EGM signals obtained respectively on bipolar ventricular and ventricular unipolar channels of one of the leads of FIG. 1.

FIG. 2 illustrates an example of $V_{bip}$ and $V_{uni}$ EGM plots respectively observed on the ventricular bipolar channel and on the ventricular unipolar channel of the configuration of FIG. 1.

Other configurations can be used, from far-field type signals (e.g., between one of the electrodes 16 or 18 and the housing 10) and near-field type signals from the non-stimulated ventricular cavity, namely the right ventricle in the example shown.

It could also be considered, in a reverse configuration, to stimulate the right ventricle and to collect bipolar and unipolar EGMs in the left ventricle. The bipolar component may then be collected for example between electrodes 30 and 32 of the left ventricular lead 28 (as referenced at 38), and the unipolar component between the tip electrode 30 (or the electrode ring 32) and the can housing of the generator 10, as referenced at 40. Alternatively, the unipolar component may also be collected between the tip electrode 30 (or the ring electrode 32) of the left ventricular lead 28 and the coil winding 36 of the right ventricular lead 12 as referenced at 42.

Figure 3:
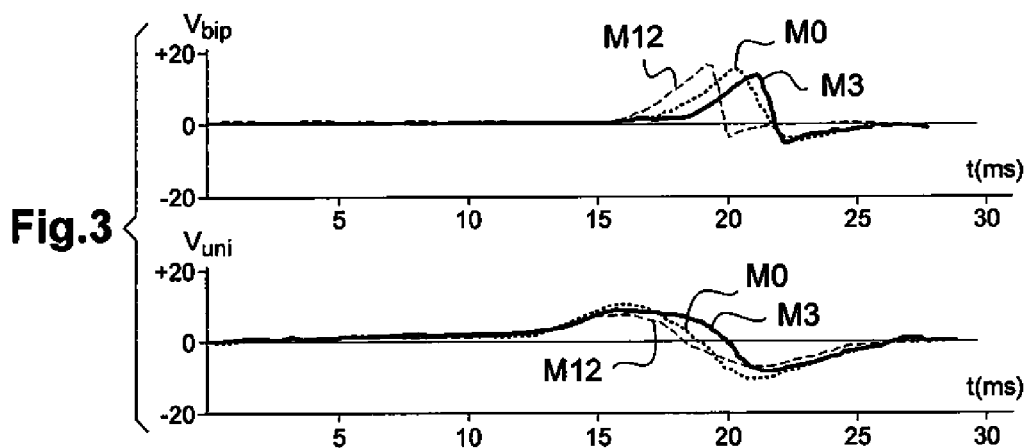
FIG. 3 is an example showing an evolution, in the long term, of unipolar and bipolar EGM signals obtained by stimulating the left ventricle and collecting the corresponding signal in the right ventricle.
Figure 4:
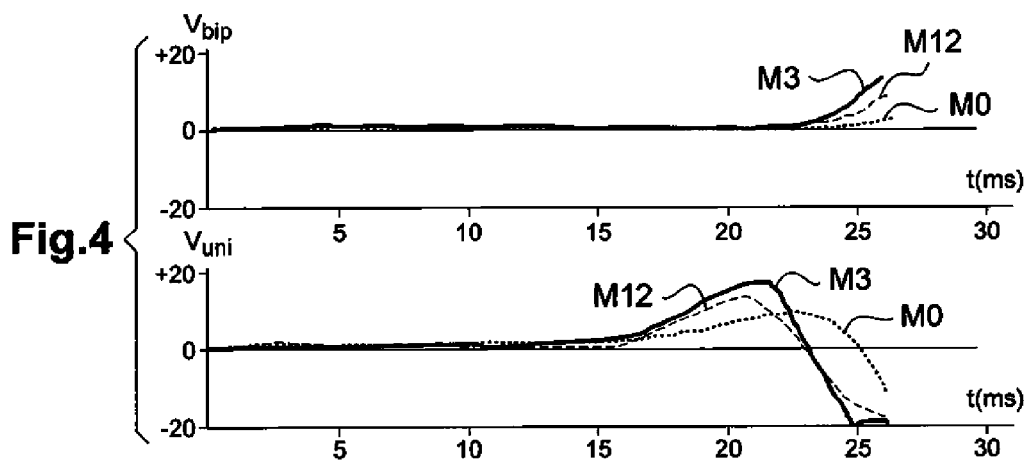
FIG. 4 is another example of EGM, of the same type as in FIG. 3.

FIGS. 3 and 4 correspond to two examples of $V_{bip}$ and $V_{uni}$ EGM signals collected with the configuration of FIG. 1, as they appear at the time of implantation (curve M0), three months after implantation (curve M3) and one year after implantation (M12 curve).

As can be seen, the shape of these signals changes over time, but for example in the case of FIG. 3 the unipolar signal does not really provide any information on the evolution in time of the conduction delay, while the bipolar signal $V_{bip}$ contains much more meaningful information. Conversely, in the case of FIG. 4, the response is very late in the bipolar signal $V_{bip}$ and it is the unipolar channel (between the coil winding 36 and the can housing 10 of the generator), which provides, in a more discriminating method, the required information.

To overcome this drawback, the disclosure proposes to combine both bipolar and unipolar components containing a unique characteristic, and more broadly, all available information in order to conduct a complete and robust assessment of the patient's condition over time.

This combination of both bipolar and unipolar signals is designed as a "heart loop" or "vectogram" (VGM), which is the representation in a two-dimensional space of one of the two EGM signals (on the ordinate) relative to one another (on the abscissa). Each cardiac cycle is then represented by a vectogram in the $\{V_{bip}, V_{uni}\}$ plan thus defined which thus ignore the temporal dimension.

It is emphasized that this "vectogram" (VGM), which is obtained from electrogram signals (EGM) from intracardiac leads, should not be confused with the "vectocardiogram" (VCG), which is itself obtained from electrocardiogram (ECG) signals from external electrodes placed on the patient's chest.

The construction of a VGM and its analysis to quantify cardiac data are described for example in Milpied et al., "Arrhythmia Discrimination in Implantable Cardioverter Defibrillators Using Support Vector Machines Applied to a New Representation of Electrograms," *IEEE Transactions on Biomedical Engineering*, June 2011, 58 (6): 1797-1803.

Analysis of a VGM for different purposes than those of the disclosure has already been proposed in particular from EP 2105843 (Sorin CRM) for discriminating between ventricular and supraventricular tachycardia, from EP 2324885 A1 (Sorin CRM) for invalidating a capture test in case of fusion, that is to say stimulation simultaneously triggered to spontaneous depolarization, from EP 2368493 A1 (Sorin CRM) for discriminating noise artifacts for the validation or invalidation of cardiac cycles to be analyzed, from EP 2742971 A1 (Sorin CRM) for determining the presence or absence of an evoked wave induced by the stimulation of a cavity, or by the EP 2742973 A1 (Sorin CRM) for detecting the possible presence of an anodal stimulation phenomenon.

Figure 5:
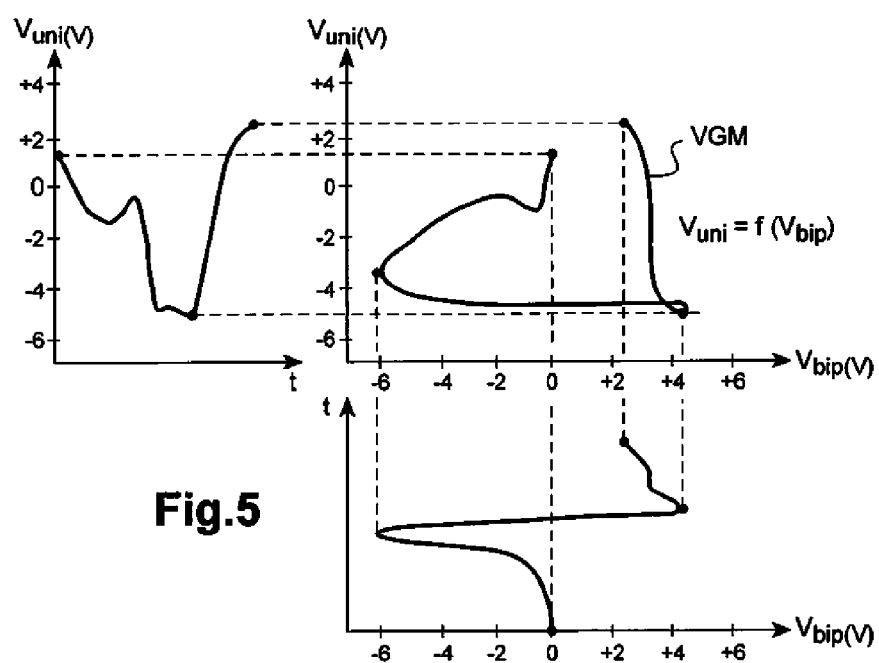
FIG. 5 shows a method of combining the bipolar and unipolar signals collected in a single ventricular cavity to construct a two-dimensional, independent of time, vectogram characteristic.

Specifically, as shown in FIG. 5, the collected EGM signals $V_{uni}(t)$ and $V_{bip}(t)$ are sampled, and the successive samples of the two components are stored and then combined to produce a parametric curve (the VGM characteristic) of the type $VGM=(V_{bip}(t), V_{uni}(t))$ or $\{x=V_{bip}(t), y=V_{uni}(t)\}$.

This curve is a curve parameterized by time, plotted on the basis of changes in one of the temporal components ($V_{uni}$) as a function of the other ($V_{bip}$). It is a vectogram (VGM) representative of the cardiac cycle to be analyzed, and is also referred to as "parametric 2D characteristic". It graphically shows the shape of a loop, wherein the time only appears in the manner in which the loop is traversed over the cycle duration.

Note that the "two-dimensional" (2D) analysis discussed here should not be understood in itself in a limiting way. The invention can indeed be applied equally to an analysis in higher order multi-dimensional space (3D or more), by extrapolating the teachings of the present description to a situation wherein EGM signals from the same cavity is collected simultaneously on three channels or more.

Figure 6:
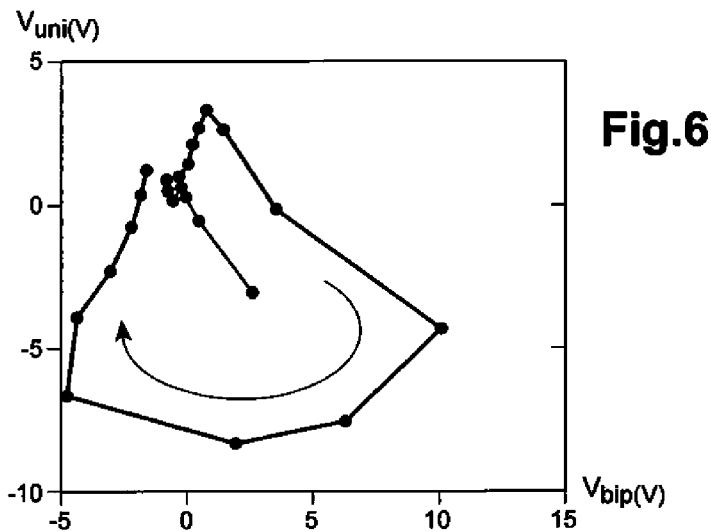
FIG. 6 is an example of a vectogram obtained for a cardiac cycle sampled at 128 Hz.

In practice, as shown in FIG. 6, sampling produces an open polygon VGM wherein each vertex corresponds to a sampling point of the measurement signal $V_{uni}$ and $V_{bip}$ EGM. In the example of FIG. 6, sampling is carried out at a frequency of 128 Hz, which gives about 20 to 25 measurement points, which are values that can be stored for analysis.

Figure 7:
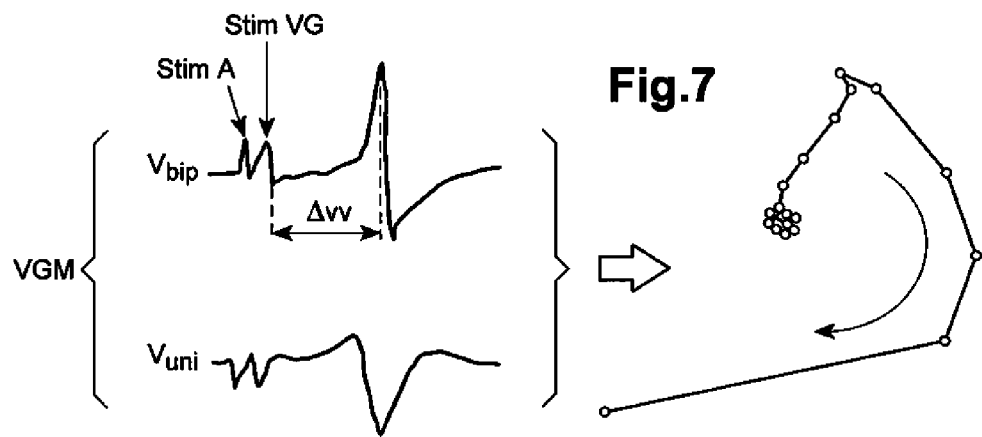
FIG. 7 illustrates examples of unipolar and bipolar signals collected in the right ventricle following a stimulation applied to the left ventricle and the corresponding vectogram constructed from these signals.

FIG. 7 illustrates more precisely the shape of $V_{uni}$ and $V_{bip}$ components in the case of a single stimulation of the left ventricle, the VGM being constructed with $V_{bip}$ and $V_{uni}$ EGMs collected in the right ventricle. In this figure it can be seen that the signal peak StimA corresponds to the atrial stimulation and StimVG corresponds to the ventricular stimulation, the interventricular conduction delay $\Delta VV$ can also be seen.

For analysis, the VGM is recorded from the instant of the ventricular stimulation peak StimVG. Advantageously, the atrioventricular delay AVD separating the atrial stimulation from the ventricular stimulation is reduced during the time of the measurement to a minimum value, for example AVD=30 ms, to ensure that there will be no fusion phenomenon with spontaneous conduction in the ventricle where the detection takes place (the right ventricle). The atrium can also be stimulated during the time of measurement to artificially lengthen the PR interval and prevent fusion.

The VGM is built periodically, for example once a day or once a week, under stable conditions (slow sinus rhythm, preferably overnight), to be stored and compared to a reference VGM created initialization therapy, and possibly updated in case of an emergency or a failure, or manually by the practitioner during a follow-up visit.

Advantageously, the VGM characteristic is stored as a vector of intrinsic descriptor parameters, describing in a condensed form the important features that will be used to analyze the VGM curve.

Figure 8:
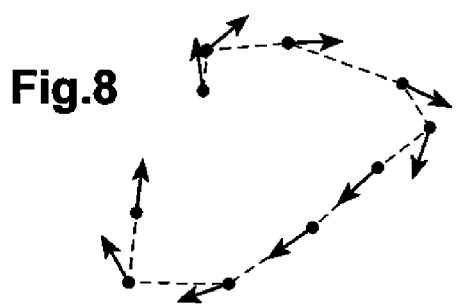
FIG. 8 is a representation of velocity vectors in an example of a sampled vectogram.

Advantageously, these intrinsic descriptor parameters of the VGM are, as shown in FIG. 8, the successive values of the magnitude of the velocity at which the VGM is traversed, calculated at each point on the VGM. At a given point, velocity is a vector data (velocity being defined by its orientation and magnitude) which for a sampled characteristic can be calculated from the previous point and the next point on the curve.

In practice, for the purpose, namely the monitoring of the evolution of the interventricular conduction delay, it appears that the velocity magnitude is a sufficient parameter, allowing significant savings in terms of computation and memory resources, a given VGM being simply stored in the form of a series (vector) of representative intrinsic descriptor parameters of the current VGM built at a given time.

To compare the current VGMs (stored as a vector of intrinsic descriptors) with a reference VGM (stored as a homologous vector of descriptor parameters), a cross-correlation between these two descriptor vectors is advantageously performed.

FIG. 9 schematically represents such a cross-correlation. The schematic function f corresponds to the vector of the intrinsic descriptor parameters of the reference VGM and the function g to the intrinsic descriptor parameters of the current VGM to be compared. The cross-correlation f*g produces a value $\tau$ of an offset to be applied to one of the descriptor parameter vectors to be aligned with the other descriptor vector.

The value of the delay $\tau$ which minimizes the cross-correlation function $f^*g(\tau)$ is regarded as an index representative of the patient's condition at the time of construction of the considered current VGM:

If this delay $\tau$ is negative, this means that a delay should be applied to the current VGM to maximize the cross-correlation function, the conduction time being shortened. If this value exceeds a predetermined threshold, for example $\tau<-10$ ms, it is then considered that the patient is in the presence of a reverse, beneficial, remodeling;

Conversely, if the delay $\tau$ is positive, it means that the delay should be applied to the reference VGM and the conduction time has lengthened, indicating a worsening of the patient's condition. Similarly, if the value exceeds a predetermined threshold, for example $\tau>10$ ms, it is considered that remodeling occurred.

FIG. 10 very generally illustrates a method in which the device of an embodiment of the disclosure is implemented.

From the collected bipolar and unipolar EGMs, a VGM is constructed (block 100). First, reference is made (block 102, detailed FIG. 11) and stored in memory (block 104). Similarly, periodically (e.g., daily) a current VGM is constructed and compared to the stored reference (block 106) to derive an indicator of the evolution of the patient's condition (remodeling, reverse remodeling, or non-scalable state).

The creation of the reference (block 102 of FIG. 10) is operated as shown in FIG. 11.

This reference is created from a plurality of representative cardiac cycles (absence of artifact, extrasystole, fusion, etc.), for example x=2 to 5 cardiac cycles, for each of which the VGM is constructed and the descriptor parameter vector is calculated (block 108). These data are then averaged (block 110) or, alternatively, one of the most representative cardiac cycles is selected to be the reference (block 112). From the averaged or selected VGM, the reference is validated (block 114), by comparing it to each cycle collected in step 108, so as to verify that the difference between this reference and each of the other cycles remains within acceptable limits.

FIG. 12 illustrates a sequence of various test operations of the current VGM (block 106 of FIG. 10) performed at regular intervals, for example every day.

The patient is stimulated for several cardiac cycles no longer in biventricular CRT stimulation, but in left ventricular stimulation only, with an AVD minimized to avoid fusion (e.g., AVD=30 ms) and a detection of the evoked wave in the right ventricle, according to both the bipolar $V_{bip}$ component and unipolar $V_{uni}$ component (block 118).

If no reference is available at this step (that is to say just after implantation), or if the stimulation parameters were modified, a reference corresponding to the current state of the patient should be created. To do this, a reference VGM is constructed (in the method explained above with reference to FIG. 11), for example, in the case of sampling at 128 Hz, for a duration of approximately 125 ms after atrial stimulation, from the sample points 10-26 (block 120). The values of the velocity magnitude at each point of the VGM are then calculated and stored for constructing a vector of current intrinsic descriptor parameters of the VGM, which in this example consists of a vector of 17 values (block 122).

If, after step 118, a reference is available in memory, the device constructs the current VGM (block 124) and constitutes the corresponding vector of current intrinsic descriptor parameters (block 126) in the same method as in blocks 120 and 122 described above.

A cross-correlation is made between the current descriptor parameters from the block 126 and the reference descriptor parameters that were previously calculated at block 122 to obtain the $\tau$ delay value that maximizes the cross-correlation function between the vector of common descriptor parameters and the vector reference descriptor parameters (block 128).

If this delay value $\tau$ is positive and greater than a given threshold, for example $\tau>10$ ms, this indicates that there was decompensation and remodeling (block 130), revealing a worsening of the patient's condition. An alert can be triggered so that appropriate action can be taken without delay (e.g., modification of CRT pacing parameters, taking medication, etc.).

If the delay $\tau$ is relatively low, for example $-10$ ms$<\tau<10$ ms, it is considered that the patient's condition has not changed significantly (block 132).

Finally, for negative values of $\tau$ below a given threshold, for example $\tau<-10$ ms, it is considered that there was reverse remodeling (block 134) and thus improvement of the patient's condition.

What is claimed is:
1. An implantable medical device comprising:
 a plurality of electrodes for detecting atrial and ventricular events;
 a memory for storing instructions;

a processor configured to execute the instructions to:
deliver stimulation via the electrodes to the right and left ventricles; and
multidimensionally measure an interventricular conduction delay, wherein the interventricular conduction delay is counted between at least one of:
a right ventricular stimulation and a spontaneous event detected in the left ventricle,
a spontaneous event detected in the left ventricle and a right ventricular stimulation, or
at least one of a right or left ventricular stimulation and a spontaneous event detected between the right and left ventricles, during the same cardiac cycle,
wherein the multidimensional measurement of the interventricular conduction delay comprises:
controlling during a cardiac cycle the stimulation methods and the detection methods so as to:
produce a stimulation of one of the right or left ventricles, and
collect in the other ventricle at least two EGM signals of endocardial electrogram and derive at least two respective distinct temporal components;
combining at least two temporal components in at least one parametric 2D characteristic representative of the cardiac cycle;
analyzing, from the 2D characteristic, or from an average of 2D characteristics collected over successive cardiac cycles, a vector of current intrinsic descriptor parameters of the 2D characteristic; and
comparing said vector of current intrinsic descriptor parameters to a homologous vector of reference descriptor parameters to derive an index representative of the evolution of a patient's condition.

2. The device of claim 1, wherein said current intrinsic descriptor parameters are parameters of the velocity vector of the 2D characteristic, considered in a plurality of respective points of the 2D characteristic.

3. The device of claim 2, wherein said parameters of the velocity vector are the respective values of the magnitude of the velocity vector.

4. The device of claim 1, wherein comparing said vector of current intrinsic descriptor parameters comprises operating a cross-correlation between i) the vector of the current intrinsic descriptor parameters and ii) the vector of the reference descriptor parameters.

5. The device of claim 4, wherein said index representative of the evolution of a patient's condition is a value of a delay ($\tau$) which maximizes an intercorrelation function between the vector of the current intrinsic descriptor parameters and the vector of the reference descriptor parameters.

6. The device of claim 5, wherein the processor is further configured to compare the delay with a predetermined threshold and trigger an alert if the predetermined threshold is crossed.

7. The device of claim 1, where the processor is further configured to temporarily shorten the atrioventricular delay of the device during an activation of the multi-dimensional measurement of the interventricular conduction delay.

8. The device of claim 1, wherein the processor is further configured to temporarily force the activation of atrial stimulation during the activation of the multidimensional measurement of the interventricular conduction delay.

9. The device of claim 1, wherein the at least two EGM signals are collected concurrently on separate respective channels.

10. The device of claim 9, wherein the at least two EGM signals collected concurrently on separate respective channels include a unipolar EGM far-field signal and a near-field EGM bipolar signal.

11. The device of claim 10, wherein the unipolar EGM far-field signal is collected between a first location comprising at least one of a proximal electrode, a distal electrode, an intermediate electrode, or a defibrillation coil electrode of a ventricular lead located in an unstimulated ventricle and a second location comprising a metal housing generator of the device.

12. The device of claim 10, wherein the unipolar EGM far-field signal is collected between a first location comprising at least one of a first proximal electrode, a first distal electrode, or a first defibrillation coil electrode of a first ventricular lead and a second location comprising at least one of a second proximal electrode, a second distal electrode, an intermediate electrode or a second defibrillation coil electrode of a second ventricular lead, wherein both the first and the second ventricular leads are located in an unstimulated ventricle.

13. The device of claim 10, wherein the unipolar EGM far-field signal is collected between a first location comprising at least one of a first proximal electrode, a first distal electrode, or a first defibrillation coil electrode of a first ventricular lead and a second location comprising at least one of a second proximal electrode, a second distal electrode, or an intermediate electrode of a second ventricular lead, wherein the first ventricular lead is located in the right ventricle and the second ventricular lead is located in the left ventricle.

14. The device of claim 10, wherein the near-field EMG bipolar signal is collected between a distal electrode and a proximal electrode of a ventricular lead located in an unstimulated ventricle.

15. The device of claim 10, wherein the near-field EMG bipolar signal is collected between a defibrillation coil and at least one of a proximal electrode or a distal electrode of a ventricular lead.

16. The device of claim 10, wherein the near-field EMG bipolar signal is collected between a distal electrode and an intermediate electrode of a left ventricular lead.

17. The device of claim 10, wherein the near-field EMG bipolar signal is collected between a proximal electrode and an intermediate electrode of a left ventricular lead.

18. The device of claim 10, wherein the near-field EMG bipolar signal is collected between a first intermediate electrode and a second intermediate electrode of a left ventricular lead.

19. An active implantable medical device for cardiac resynchronization by biventricular stimulation, comprising:
a memory for storing instructions;
a processor configured to execute the instructions to:
deliver stimulation via electrodes to the right and left ventricles; and
multidimensionally measure an interventricular conduction delay, wherein the interventricular conduction delay is counted between at least one of:
a right ventricular stimulation and a spontaneous event detected in the left ventricle,
a spontaneous event detected in the left ventricle and a right ventricular stimulation, or
at least one of a right or left ventricular stimulation and a spontaneous event detected between the right and left ventricles, during the same cardiac cycle, wherein the multidimensional measurement of the interventricular conduction delay comprises:
controlling during a cardiac cycle the stimulation methods and the detection methods so as to:
produce a stimulation of one of the right or left ventricles, and
collect in the other ventricle at least two EGM signals of endocardial electrogram and derive at least two respective distinct temporal components;
combining at least two temporal components in at least one parametric 2D characteristic representative of the cardiac cycle;
analyzing, from the 2D characteristic, or from an average of 2D characteristics collected over successive cardiac cycles, a vector of current intrinsic descriptor parameters of the 2D characteristic; and
comparing said vector of current intrinsic descriptor parameters to a homologous vector of reference descriptor parameters to derive an index representative of the evolution of a patient's condition.

20. A method of cardiac resynchronization by biventricular stimulation, comprising:
delivering stimulation via electrodes to the right and left ventricles; and
multidimensionally measuring an interventricular conduction delay, wherein the interventricular conduction delay is counted between at least one of:
a right ventricular stimulation and a spontaneous event detected in the left ventricle,
a spontaneous event detected in the left ventricle and a right ventricular stimulation, or
at least one of a right or left ventricular stimulation and a spontaneous event detected between the right and left ventricles, during the same cardiac cycle,
wherein multidimensionally measuring the interventricular conduction delay comprises:
controlling during a cardiac cycle the stimulation methods and the detection methods so as to:
produce a stimulation of one of the right or left ventricles, and
collect in the other ventricle at least two EGM signals of endocardial electrogram and derive at least two respective distinct temporal components;
combining at least two temporal components in at least one parametric 2D characteristic representative of the cardiac cycle;
analyzing, from the 2D characteristic, or from an average of 2D characteristics collected over successive cardiac cycles, a vector of current intrinsic descriptor parameters of the 2D characteristic; and
comparing said vector of current intrinsic descriptor parameters to a homologous vector of reference descriptor parameters to derive an index representative of the evolution of a patient's condition.

* * * * *